(12) United States Patent
Imai

(10) Patent No.: US 7,118,939 B2
(45) Date of Patent: Oct. 10, 2006

(54) MANUFACTURING METHOD AND MANUFACTURING APPARATUS FOR SEMICONDUCTOR DEVICE

(75) Inventor: Takahiro Imai, Sakata (JP)

(73) Assignee: Seiko Epson Corporation, Tokyo (JP)

( * ) Notice: Subject to any disclaimer, the term of this patent is extended or adjusted under 35 U.S.C. 154(b) by 87 days.

(21) Appl. No.: 11/048,780

(22) Filed: Feb. 3, 2005

(65) Prior Publication Data

US 2005/0183295 A1     Aug. 25, 2005

(30) Foreign Application Priority Data

Feb. 6, 2004     (JP)     ............... 2004-030861

(51) Int. Cl.
*H01L 21/44*     (2006.01)
(52) U.S. Cl. ............... 438/108; 438/612; 438/E21.499; 29/833; 29/834; 228/108.22
(58) Field of Classification Search ................. 438/15, 438/107, 108, 612; 29/833, 834; 228/180.22
See application file for complete search history.

(56) References Cited

U.S. PATENT DOCUMENTS 6,699,737 B1 *   3/2004   Tojo et al. ................. 438/119

FOREIGN PATENT DOCUMENTS

| JP | A 2001-298046 | 10/2001 |
|---|---|---|
| JP | A 2003-124262 | 4/2003 |

* cited by examiner

*Primary Examiner*—Quoc Hoang
(74) *Attorney, Agent, or Firm*—Oliff & Berridge, PLC (57) ABSTRACT

A formation surface of electrodes and a formation surface of leads are imaged along an axis which intersects an XY plane at right angles. A projected image of the formation surface of the electrodes and the formation surface of the leads is obtained, the projected image being projected onto a plane which intersects the Z axis at right angles. A difference between an image of one of the electrodes and an image of one of the leads in the projected image is calculated. A deformation value of at least one of a substrate and a semiconductor chip due to expansion or shrinkage is calculated, the deformation value being necessary for eliminating the difference. A change in temperature of at least one of the substrate and the semiconductor chip is calculated the change in temperature being necessary for obtaining the deformation value. The temperature of at least one of the substrate and the semiconductor chip is changed based on the change in temperature.

8 Claims, 5 Drawing Sheets

MANUFACTURING METHOD AND MANUFACTURING APPARATUS FOR SEMICONDUCTOR DEVICE

Japanese Patent Application No. 2004-30861, filed on Feb. 6, 2004, is hereby incorporated by reference in its entirety.

BACKGROUND OF THE INVENTION

The present invention relates to a manufacturing method and a manufacturing apparatus for a semiconductor device.

As a semiconductor device in which a semiconductor chip including bump electrodes such as Au bumps is mounted face down on a flexible film substrate, a tape automated bonding (TAB) or a tape carrier package (TCP) has been known.

The flexible film substrate used for TAB or TCP is generally manufactured by forming a plurality of interconnect patterns made of Cu on the surface of an insulating film made of a polyimide resin or the like. Therefore, since the insulating film expands and shrinks due to the temperature or moisture in the atmosphere, an error occurs in the pitch of the interconnect pattern.

For example, Japanese Patent Application Laid-open No. 2003-124262 discloses a technology of providing pitch correction to an inner interconnect pattern in advance as a means for solving the difference in pitch caused by heating during bonding.

However, since the coefficient of expansion varies depending on the thickness of the insulating film (inter-lot variation), it is difficult to achieve scaling down merely by providing the above-mentioned pitch correction.

BRIEF SUMMARY OF THE INVENTION

According to a first aspect of the present invention, there is provided a method of manufacturing a semiconductor device, the method comprising:

(a) disposing a substrate on which a plurality of leads are formed on an XY plane in a three-dimensional coordinate system consisting of XYZ axes;

(b) disposing a semiconductor chip including a plurality of electrodes so that a formation surface of the electrodes faces a formation surface of the leads of the substrate with an interval;

(c) positioning the leads and the electrodes so that the leads and the electrodes respectively face each other; and (d) electrically connecting the leads with the electrodes, wherein the step (c) includes:

($c_1$) imaging the formation surface of the electrodes and the formation surface of the leads along an axis which intersects the XY plane at right angles;

($c_2$) obtaining a projected image of the formation surface of the electrodes and the formation surface of the leads projected onto a plane which intersects the Z axis at right angles;

($c_3$) calculating a difference between an image of one of the electrodes and an image of one of the leads in the projected image;

($c_4$) calculating a deformation value of at least one of the substrate and the semiconductor chip due to expansion or shrinkage necessary for eliminating the difference;

($c_5$) calculating a change in temperature of at least one of the substrate and the semiconductor chip necessary for obtaining the deformation value; and ($c_6$) changing the temperature of at least one of the substrate and the semiconductor chip based on the change in temperature.

According to a second aspect of the present invention, there is provided a manufacturing apparatus for a semiconductor device, the apparatus comprising:

a stage for disposing a substrate on which a plurality of leads are formed on an XY plane in a three-dimensional coordinate system consisting of XYZ axes;

a carrier for disposing a semiconductor chip including a plurality of electrodes and the substrate so that a formation surface of the electrodes relatively faces a formation surface of the leads of the substrate with an interval;

an adjuster for positioning the leads and the electrodes so that the leads and the electrodes respectively face each other; and a press for relatively pressing the electrodes against the leads, wherein the adjuster includes:

first means for imaging the formation surface of the electrodes and the formation surface of the leads along an axis which intersects the XY plane at right angles;

second means for obtaining a projected image of the formation surface of the electrodes and the formation surface of the leads projected onto a plane which intersects the Z axis at right angles;

third means for calculating a difference between an image of one of the electrodes and an image of one of the leads in the projected image;

fourth means for calculating a deformation value of at least one of the substrate and the semiconductor chip due to expansion or shrinkage necessary for eliminating the difference;

fifth means for calculating a change in temperature of at least one of the substrate and the semiconductor chip necessary for obtaining the deformation value; and sixth means for changing the temperature of at least one of the substrate and the semiconductor chip based on the change in temperature.

DETAILED DESCRIPTION OF THE EMBODIMENTS

An objective of the embodiments of the present invention is to provide a technology capable of connecting leads of a substrate with electrodes of a semiconductor chip with high accuracy.

(1) According to one embodiment of the present invention, there is provided a method of manufacturing a semiconductor device, the method comprising:

(a) disposing a substrate on which a plurality of leads are formed on an XY plane in a three-dimensional coordinate system consisting of XYZ axes;

(b) disposing a semiconductor chip including a plurality of electrodes so that a formation surface of the electrodes faces a formation surface of the leads of the substrate with an interval;

(c) positioning the leads and the electrodes so that the leads and the electrodes respectively face each other; and (d) electrically connecting the leads with the electrodes, wherein the step (c) includes:

($c_1$) imaging the formation surface of the electrodes and the formation surface of the leads along an axis which intersects the XY plane at right angles;

($c_2$) obtaining a projected image of the formation surface of the electrodes and the formation surface of the leads projected onto a plane which intersects the Z axis at right angles;

($c_3$) calculating a difference between an image of one of the electrodes and an image of one of the leads in the projected image;

($c_4$) calculating a deformation value of at least one of the substrate and the semiconductor chip due to expansion or shrinkage necessary for eliminating the difference;

($c_5$) calculating a change in temperature of at least one of the substrate and the semiconductor chip necessary for obtaining the deformation value; and ($c_6$) changing the temperature of at least one of the substrate and the semiconductor chip based on the change in temperature.

In this embodiment, a minute connection can be achieved by enabling positioning through observation, even when the electrodes and the leads are reduced in size and fine adjustment of the change in pitch due to heating is necessary.

(2) In the step ($c_1$) of this method of manufacturing a semiconductor device, the formation surface of the electrodes and the formation surface of the leads may be imaged at the same time during the imaging.

(3) In the step ($c_1$) of this method of manufacturing a semiconductor device, the imaging may be performed by using light in an infrared wavelength region.

(4) In this method of manufacturing a semiconductor device, the step ($c_5$) may include calculating an increase in temperature of at least one of the substrate and the semiconductor chip.

(5) According to one embodiment of the present invention, there is provided a manufacturing apparatus for a semiconductor device, the apparatus comprising:

a stage for disposing a substrate on which a plurality of leads are formed on an XY plane in a three-dimensional coordinate system consisting of XYZ axes;

a carrier for disposing a semiconductor chip including a plurality of electrodes and the substrate so that a formation surface of the electrodes relatively faces a formation surface of the leads of the substrate with an interval;

an adjuster for positioning the leads and the electrodes so that the leads and the electrodes respectively face each other; and a press for relatively pressing the electrodes against the leads, wherein the adjuster includes:

first means for imaging the formation surface of the electrodes and the formation surface of the leads along an axis which intersects the XY plane at right angles;

second means for obtaining a projected image of the formation surface of the electrodes and the formation surface of the leads projected onto a plane which intersects the Z axis at right angles;

third means for calculating a difference between an image of one of the electrodes and an image of one of the leads in the projected image;

fourth means for calculating a deformation value of at least one of the substrate and the semiconductor chip due to expansion or shrinkage necessary for eliminating the difference;

fifth means for calculating a change in temperature of at least one of the substrate and the semiconductor chip necessary for obtaining the deformation value; and sixth means for changing the temperature of at least one of the substrate and the semiconductor chip based on the change in temperature.

(6) In this manufacturing apparatus for a semiconductor device, the first means may image the formation surface of the electrodes and the formation surface of the leads at the same time.

(7) In this manufacturing apparatus for a semiconductor device, the first means may perform imaging by using light in an infrared wavelength region.

(8) In this manufacturing apparatus for a semiconductor device, the fifth means may calculate an increase in temperature of at least one of the substrate and the semiconductor chip.

Figure 1A:
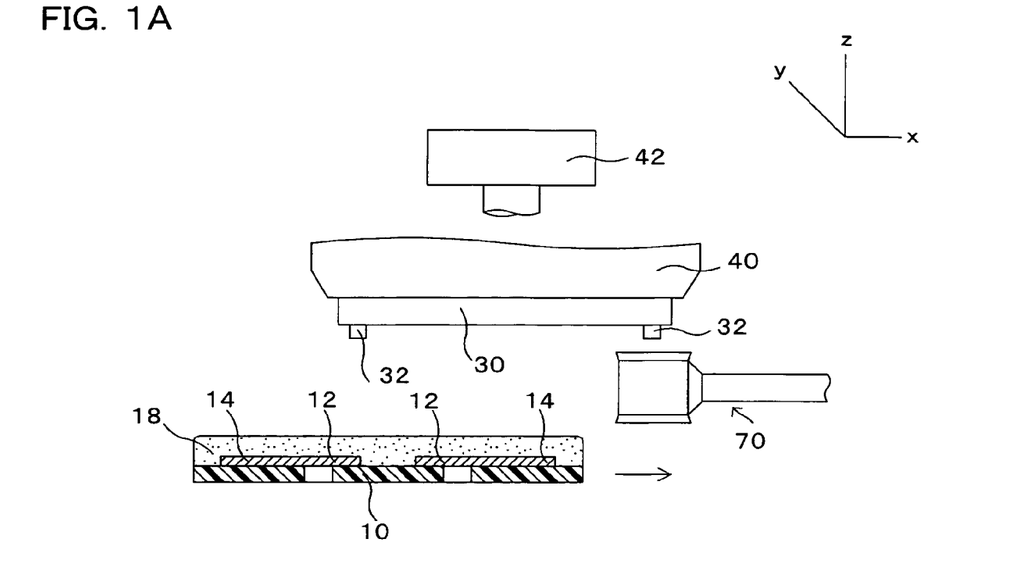
FIGS. 1A to 1C are diagrams illustrative of a method of manufacturing a semiconductor device according to one embodiment of the present invention.
Figure 1B:
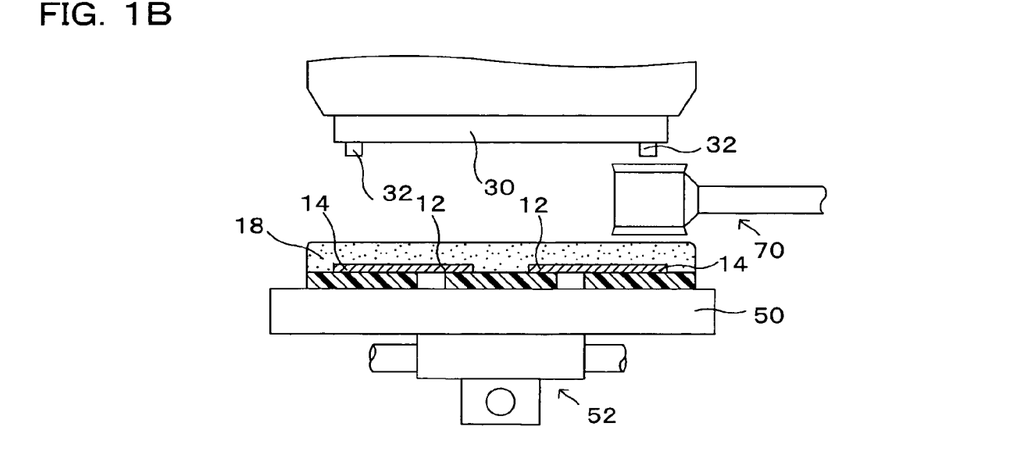
Figure 1C:
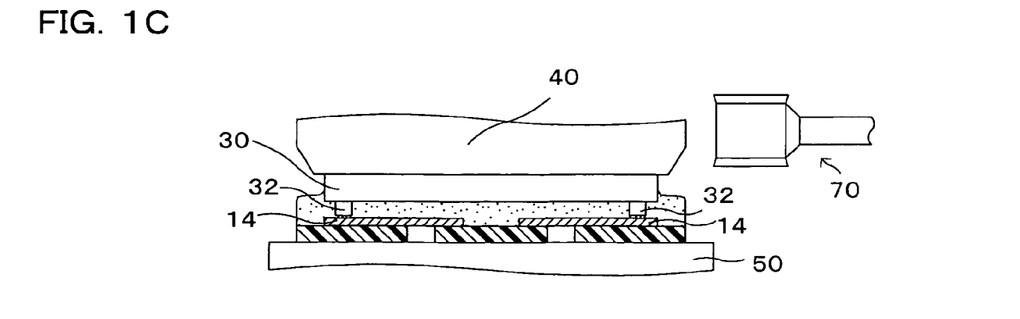

The embodiments of the present invention will be described below with reference to the drawings. FIGS. 1A to 1C are diagrams illustrative of a method of manufacturing a semiconductor device according to one embodiment of the present invention.

In this embodiment, a substrate 10 is provided (see FIG. 1A). The substrate 10 is formed of an organic or resin material or the like and exhibits flexibility. The material for the substrate 10 is not limited insofar as the substrate 10 exhibits flexibility. As the material for the substrate 10, polyethyleneterephthalate (PET), a polyimide resin, polyether sulfone (PES), polyether ether ketone (PEEK), and the like can be given. Leads 12 are formed on one surface of the substrate 10. An interconnect pattern may be formed on the other surface of the substrate 10 in addition to the leads 12 formed on one surface of the substrate 10. The interconnect pattern formed on the other surface is not an essential requirement for the present invention. The leads 12 may be formed by causing a conductive film such as a copper film to adhere to the substrate 10 by sputtering or the like, and etching the conductive film. In this case, the leads 12 are directly formed on the substrate 10 to form a two-layer substrate. A land 14 is provided to the lead 12 to facilitate bonding with an electrode 32 of a semiconductor chip 30. A bump may be formed on the land 14. The leads 12 may be covered with an anisotropic conductive film sheet or the like as an adhesive 18.

The method of manufacturing a semiconductor device according to this embodiment is described below. As shown in FIG. 1A, the substrate 10 and the semiconductor chip 30 are disposed so that the surface of the substrate 10 on which the leads 12 are formed and the surface of the semiconductor chip 30 on which the electrodes 32 are formed face in opposite directions in which the surfaces face each other when the surfaces are moved parallel. In other words, the surface of the substrate 10 opposite to the surface on which the leads 12 are formed and the surface of the semiconductor chip 30 on which the electrodes 32 are formed face in the same direction and are positioned so that the surfaces do not overlap on a single plane in a plan view.

In FIG. 1B, a top-and-bottom simultaneous imaging camera 70 is disposed to face in the directions in which the top-and-bottom simultaneous imaging camera 70 can face the surface of the substrate 10 on which the leads 12 are formed and the surface of the semiconductor chip 30 on which the electrodes 32 are formed, and is disposed to actually face these surfaces. Specifically, the top-and-bottom simultaneous imaging camera 70 is disposed to face the surface of the substrate 10 on which the leads 12 are formed. The top-and-bottom simultaneous imaging camera 70 is also disposed to face the surface of the semiconductor chip 30 on which the electrodes 32 are formed.

The substrate 10 and the semiconductor chip 30 are respectively held by a heater stage 50 and a bonding tool 40 so that the substrate 10 and the semiconductor chip 30 can be moved parallel along the surface on which the leads 12 are formed or the surface on which the electrodes 32 are formed.

The top-and-bottom simultaneous imaging camera 70 images the formation surface of the leads 12 and the formation surface of the electrodes 32 in this state along an axis which intersects the XY plane at right angles. The resulting image is a projected image of the formation surface of the leads 12 and the formation surface of the electrodes 32 projected onto a plane which intersects the Z axis at right angles. A computer performs predetermined processing based on the projected image, and positions the leads 12 and the electrodes 32 using the bonding tool 40 and the heater stage 50 so that the leads 12 and the electrodes 32 respectively face each other.

In FIG. 1C, the lands 14 and the electrodes 32 are subjected to face down mounting. In FIGS. 1A and 1B, the position of the top-and-bottom simultaneous imaging camera 70 is fixed during imaging. It is preferable that the top-and-bottom simultaneous imaging camera 70 be moved parallel to the formation surfaces of the leads and the electrodes during face down mounting as shown in FIG. 1C in order to enable positioning.

Figure 2:
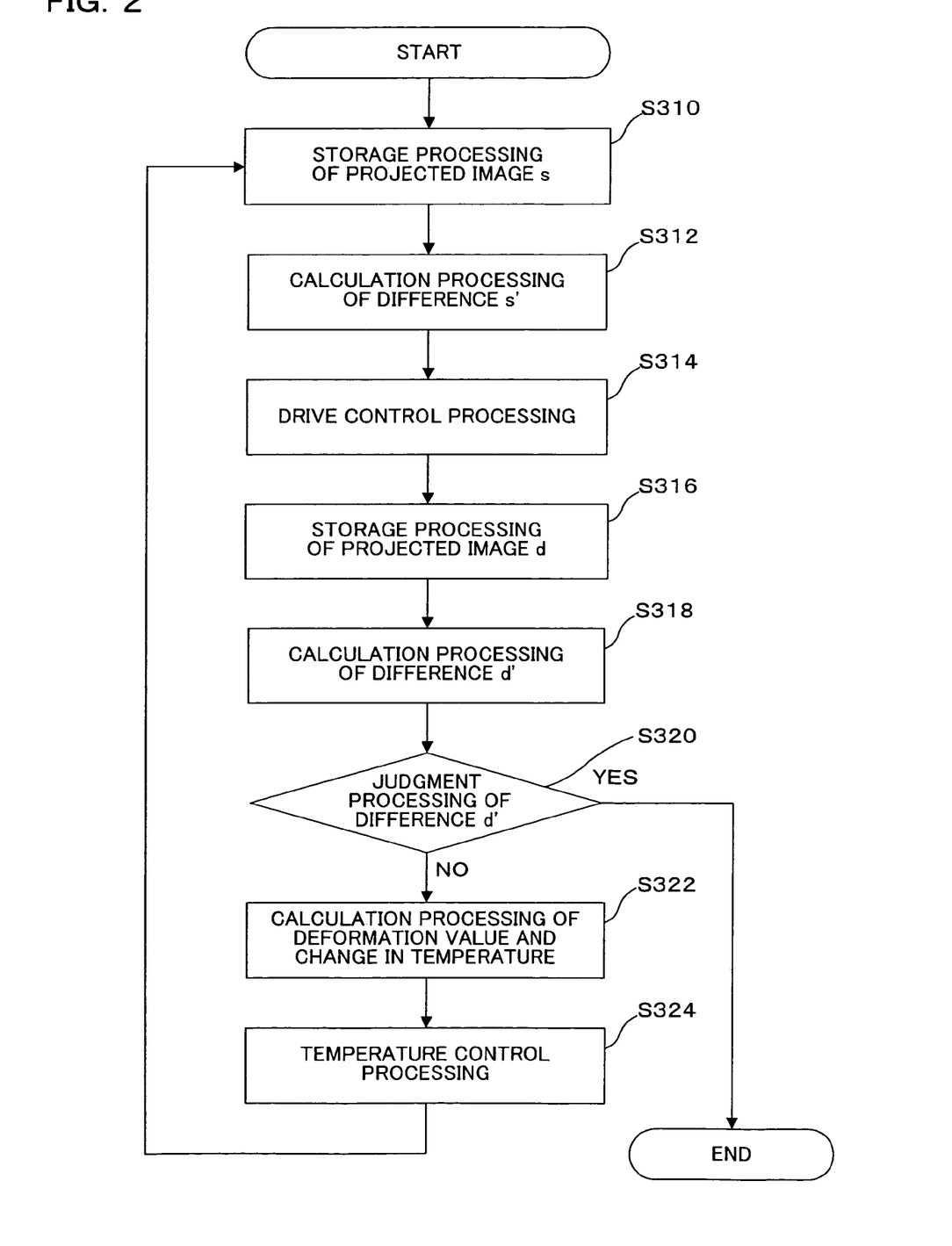
FIG. 2 is a positioning flowchart according to one embodiment of the present invention.

A process of positioning the leads 12 and the electrodes 32, so that the leads 12 and the electrodes 32 respectively face each other, by software using the projected image of the electrode formation surface and the lead formation surface imaged by the top-and-bottom simultaneous imaging camera 70 according to this embodiment is described below in detail. FIG. 2 is a positioning flowchart in this embodiment.

As shown in FIG. 2, in this embodiment, the formation surface of a predetermined electrode 232 of the semiconductor chip 30 and the formation surface of a lead 212 are imaged at the same time in a step S3 10 using the top-and-bottom simultaneous imaging camera 70 along an axis which intersects the XY plane at right angles. A projected image s of the formation surface of the electrode 232 and the formation surface of the lead 212 projected onto a plane which intersects the Z axis at right angles is stored.

Figure 5:
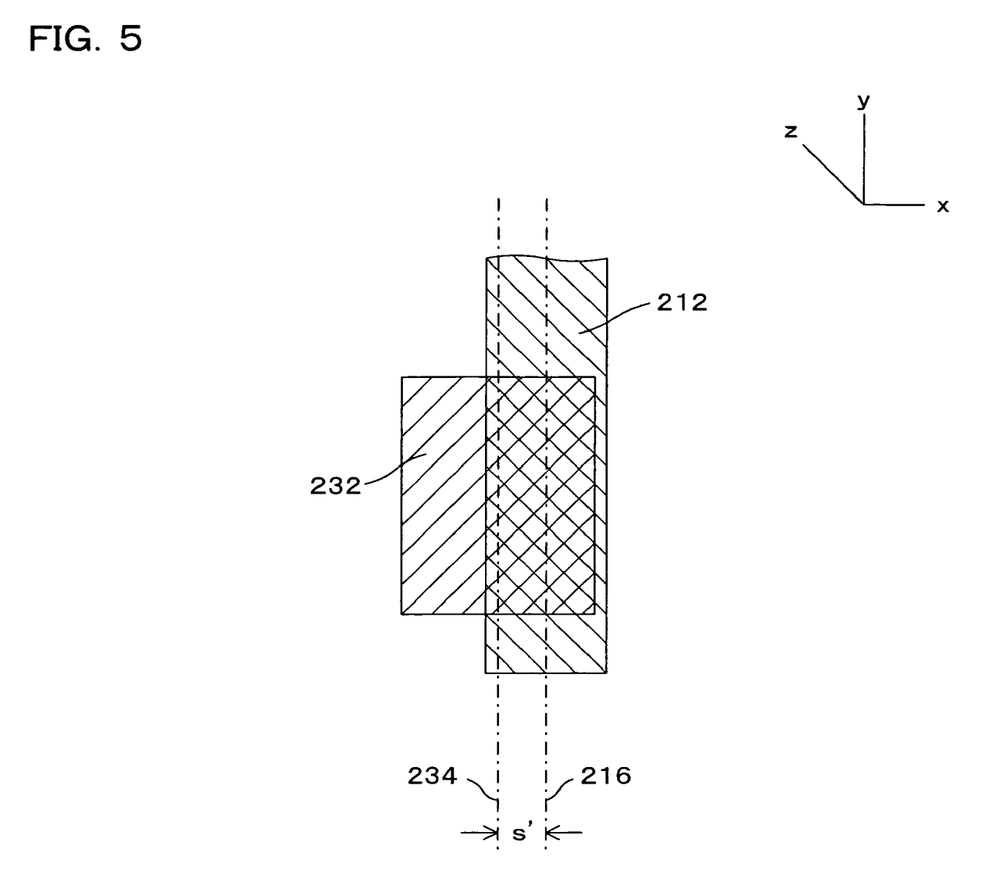
FIG. 5 is a diagram illustrative of a difference s' in a projected image according to one embodiment of the present invention.

In a step S312, the difference s' between the image of the electrode 232 and the image of the lead 212 in the projected image s stored in the step S310 is calculated. In more detail, the X coordinate position of an electrode centerline 234 which is the centerline of the electrode 232 and the X coordinate position of a lead centerline 216 which is the centerline of the lead 212 are calculated by image-processing the projected image s, and the difference s' (see FIG. 5), which is the difference between the electrode centerline 234 and the lead centerline 216 in the X coordinate direction, is calculated.

In a step S314, the displacement amount of the substrate 10 in the X coordinate direction necessary for decreasing the difference s' calculated in the step S312 to "0" is calculated. The heater stage 50 on which the substrate 10 is disposed is moved using a carrier 52 based on the displacement amount.

In a step S316, the formation surface of the electrode 32 and the formation surface of the lead 12 differing from the electrode 232 of the semiconductor chip 30 and the lead 212 imaged in the step S310 are imaged at the same time using the top-and-bottom simultaneous imaging camera 70 along an axis which intersects the XY plane at right angles. A projected image d of the formation surface of the electrode 32 and the formation surface of the lead 12 projected onto a plane which intersects the Z axis at right angles is stored.

Figure 4:
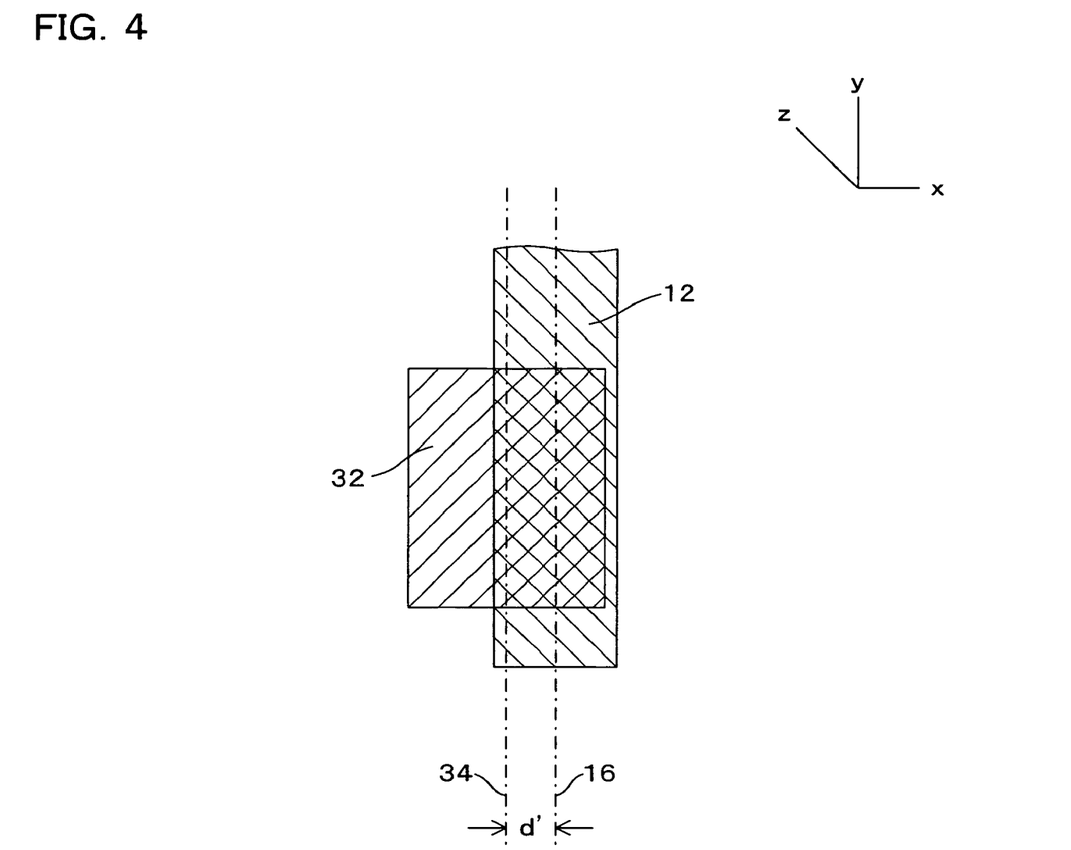
FIG. 4 is a diagram illustrative of a difference d' in a projected image according to one embodiment of the present invention.

In a step S318, the difference d' between the image of the electrode 32 and the image of the lead 12 in the projected image d stored in the step S316 is calculated. In more detail, the X coordinate position of an electrode centerline 34 which is the centerline of the electrode 32 and the X coordinate position of a lead centerline 16 which is the centerline of the lead 12 are calculated by image-processing the projected image d, and the difference d' (see FIG. 4) which is the difference between the electrode centerline 34 and the lead centerline 16 in the X coordinate direction is calculated.

In a step S320, the state of the difference d' between the electrode centerline 34 in the image of the electrode 32 and the lead centerline 16 in the image of the lead 12 is judged. When it is judged that the difference d' is not "0" ("NO"), the processing proceeds to a step S322. The processing is terminated when the difference d' is "0" ("YES").

In the step S322, the deformation value of at least one of the substrate 10 and the semiconductor chip 30 due to expansion or shrinkage necessary for decreasing the difference d' between the electrode centerline 34 in the image of the electrode 32 and the lead centerline 16 in the image of the lead 12 calculated in the step S318 to "0" is calculated. A change in temperature of at least one of the substrate 10 and the semiconductor chip 30 necessary for obtaining the deformation value is calculated using the coefficient of linear expansion of each of the substrate 10 and the semiconductor chip 30 and the like.

In a step S324, the temperature of at least one of the heater stage 50 on which the substrate 10 is disposed and the bonding tool 40 on which the semiconductor chip 30 is disposed is controlled based on the change in temperature calculated in the step S322.

The processing is then returned to the step S310, and is repeated until the difference d' becomes "0" in the step S320.

Figure 3:
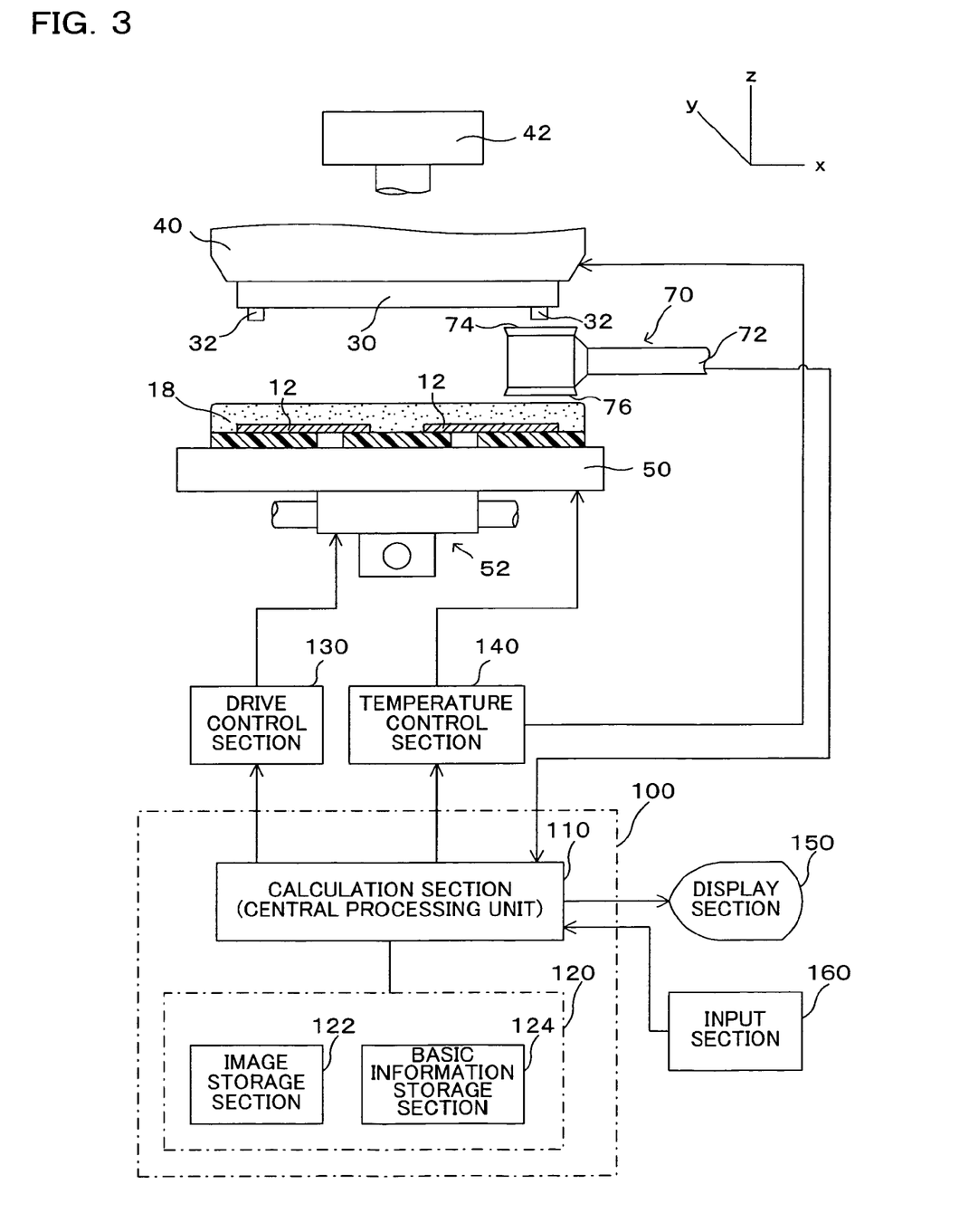
FIG. 3 is a diagram illustrative of a manufacturing apparatus for a semiconductor device according to one embodiment of the present invention.

This is the method of manufacturing a semiconductor device according to one embodiment of the present invention. A manufacturing apparatus for the semiconductor device is described below. FIG. 3 is a diagram illustrative of a manufacturing apparatus for a semiconductor device according to one embodiment of the present invention.

As shown in FIG. 3, in this embodiment, the manufacturing apparatus includes the bonding tool 40, a press 42, the heater stage 50 as a stage, the carrier 52, the top-and-bottom simultaneous imaging camera 70 (first means), a computer 100, and a temperature control section 140 (sixth means) as an adjuster, and a drive control section 130. The computer 100 further includes a calculation section 110 as a third means, a fourth means, and a fifth means, and a storage section 120 as a second means.

The bonding tool 40 is moved in the direction Z by the press 42, and relatively presses the electrodes 32 against the leads 12. The bonding tool 40 changes the temperature of the semiconductor chip 30 using a heater means (not shown).

The press 42 is connected with the bonding tool 40, and causes the electrodes 32 to be pressed against the leads 12 via the bonding tool 40 by moving the bonding tool 40 in the direction Z.

The heater stage 50 places the substrate 10 on which the leads 12 are formed on the XY plane in the three-dimensional coordinate system consisting of the XYZ axes. The heater stage 50 changes the temperature of the substrate 10 using a heater means (not shown).

The carrier 52 moves the heater stage 50 parallel to the surface of the substrate 10 on which the leads 12 are formed.

The top-and-bottom simultaneous imaging camera 70 images the formation surface of the electrodes 32 and the formation surface of the leads 12 along an axis which intersects the XY plane at right angles. The resulting image is a projected image of the formation surface of the electrodes 32 and the formation surface of the leads 12 projected onto a plane which intersects the Z axis at right angles. The top-and-bottom simultaneous imaging camera 70 is disposed between the bonding tool 40 and the heater stage 50 when the bonding tool 40 and the heater stage 50 are placed at the bonding position. The top-and-bottom simultaneous imaging camera 70 images the formation surface of the electrodes 32 and the formation surface of the leads 12 at the same time. The top-and-bottom simultaneous imaging camera 70 is preferable since a sufficient amount of transmitted light is obtained even when imaging the leads 12 covered with the adhesive 18 by using light in the infrared wavelength region. The position of the top-and-bottom simultaneous imaging camera 70 is fixed during imaging. However, the top-and-bottom simultaneous imaging camera 70 is held by a slide means (not shown) during face down mounting so that the top-and-bottom simultaneous imaging camera 70 can be moved parallel to the formation surfaces of the leads and the electrodes. The top-and-bottom simultaneous imaging camera 70 uses two mirrors in a body provided on the end of a rod 72 and leads images to one camera using the two mirrors. The top-and-bottom simultaneous imaging camera 70 includes an upper camera window 74 as an upper imaging section on the upper surface, and a lower camera window 76 as a lower imaging section on the lower surface. The top-and-bottom simultaneous imaging camera may be formed by disposing two CCD cameras so that the back surfaces face each other.

The drive control section 130 is connected with the carrier 52 of the heater stage 50. The drive control section 130 controls drive of the heater stage 50, on which the substrate 10 is disposed, in the X coordinate direction using the carrier 52 in response to an instruction from the calculation section 110.

The temperature control section 140 is connected with the heater means (not shown) of the bonding tool 40 and the heater stage 50. The temperature control section 140 changes the temperature of at least one of the semiconductor chip 30 and the substrate 10 using the heater means (not shown) of the bonding tool 40 and the heater stage 50 in response to an temperature change instruction from the calculation section 110.

The calculation section 110 calculates the difference s' between the image of the electrode 232 and the image of the lead 212 in the projected image s stored in the image storage section 122. In more detail, the calculation section 110 calculates the X coordinate position of the electrode centerline 234 which is the centerline of the electrode 232 and the X coordinate position of the lead centerline 216 which is the centerline of the lead 212 by image-processing the projected image s, and calculates the difference s' (see FIG. 5) which is the difference between the electrode centerline 234 and the lead centerline 216 in the X coordinate direction. The calculation section 110 calculates the displacement amount of the substrate 10 in the X coordinate direction necessary for decreasing the difference s' to "0". The calculation section 110 indicates the displacement amount to the drive control section 130.

The calculation section 110 calculates the difference d' between the image of the electrode 32 and the image of the lead 12 in the projected image d stored in the image storage section 122. In more detail, the calculation section 110 calculates the X coordinate position of the electrode centerline 34 which is the centerline of the electrode 32 and the X coordinate position of the lead centerline 16 which is the centerline of the lead 12 by image-processing the projected image d, and calculates the difference d' (see FIG. 4) which is the difference between the electrode centerline 34 and the lead centerline 16 in the X coordinate direction. The calculation section 110 calculates the deformation value of at least one of the substrate 10 and the semiconductor chip 30 due to expansion or shrinkage necessary for decreasing the difference d' to "0". The calculation section 110 calculates a change in temperature of at least one of the substrate 10 and the semiconductor chip 30 necessary for obtaining the deformation value using the coefficient of linear expansion of each of the substrate 10 and the semiconductor chip 30 and the like stored in a basic information storage section 124.

The storage section 120 includes a storage medium (recording medium) such as a RAM, a ROM, or a magnetic disk from which data can be read. The storage medium is formed by a magnetic or optical recording medium, a semiconductor memory, or the like. The storage section 120 includes the image storage section 122 and the basic information storage section 124.

The image storage section 122 stores an image projected onto a plane which intersects the Z axis at right angles from the top-and-bottom simultaneous imaging camera 70 which images the electrode formation surface and the lead formation surface along an axis which intersects the XY plane at right angles. The image storage section 122 also stores an image subjected to various types of image processing, if necessary.

The basic information storage section 124 acquires basic information on the substrate 10 and the semiconductor chip 30 from a data server (not shown) through a network. As the basic information to be acquired, the coefficient of linear expansion of each of the substrate 10 and the semiconductor chip 30 and the like can be given.

The calculation section 110 is connected with the top-and-bottom simultaneous imaging camera 70, the drive control section 130, the temperature control section 140, a display section 150, and an input section 160.

The display section 150 is formed by a cathode-ray tube (CRT), a liquid crystal display, or the like, and displays an operation screen, a data input screen, or the like. The display section 150 may display images of the formation surface of the electrodes 32 and the formation surface of the leads 12 imaged by the top-and-bottom simultaneous imaging camera 70, the processing state in the middle of image processing, or images of the shapes of the formation surface of the electrodes 32 and the formation surface of the leads 12 finally recognized.

The input section 160 may be connected with a keyboard for inputting characters and figures, a mouse for performing various operations using a cursor displayed on a screen of the display section 150, a host computer through a network, and the like.

According to this embodiment, the difference d' between the electrode centerline 34 in the image of the electrode 32 and the lead centerline 16 in the image of the lead 12 can be decreased to "0" by changing the temperature of at least one of the substrate 10 and the semiconductor chip 30, whereby the leads 12 and the electrodes 32 can be positioned so that the leads 12 and the electrodes 32 respectively face each other. This enables the position of the lead 12 to coincide with the position of the electrode 32 which should be connected with that lead 12 with high accuracy, even if the substrate 10 expands or apparently shrinks due to heat applied from the bonding tool 40. Specifically, an open failure in which the lead 12 is not in contact with the electrode 32 or a short circuit failure in which two adjacent electrodes 32 come in contact through one lead 12 can be reliably prevented. An example of using an automatic recognition positioning apparatus (or step) is described above. However, the present invention may be applied to a manual positioning apparatus (apparatus which allows an operator to perform positioning while watching a camera image on a display). This enables highly accurate bonding to be performed using a simple apparatus without using expensive equipment.

The present invention is not limited to the above-described embodiments, and various modifications can be made. For example, the present invention includes various other configurations substantially the same as the configurations described in the embodiments (in function, method and effect, or in objective and effect, for example). The present invention also includes a configuration in which an unsubstantial portion in the described embodiments is replaced. The present invention also includes a configuration having the same effects as the configurations described in the embodiments, or a configuration able to achieve the same objective. Further, the present invention includes a configuration in which a publicly known technique is added to the configurations in the embodiments. Further, the present invention includes a configuration in which part of the technical items described in the embodiments is excluded. The present invention also includes a configuration in which a conventional art is excluded from the above-described embodiments.

Although only some embodiments of the present invention have been described in detail above, those skilled in the art will readily appreciate that many modifications are possible in the embodiments without departing from the novel teachings and advantages of this invention. Accordingly, all such modifications are intended to be included within the scope of this invention.

What is claimed is:

1. A method of manufacturing a semiconductor device, the method comprising:
   (a) disposing a substrate on which a plurality of leads are formed on an XY plane in a three-dimensional coordinate system consisting of XYZ axes;
   (b) disposing a semiconductor chip including a plurality of electrodes so that a formation surface of the electrodes faces a formation surface of the leads of the substrate with an interval;
   (c) positioning the leads and the electrodes so that the leads and the electrodes respectively face each other; and
   (d) electrically connecting the leads with the electrodes, wherein the step (c) includes:
   ($c_1$) imaging the formation surface of the electrodes and the formation surface of the leads along an axis which intersects the XY plane at right angles;
   ($c_2$) obtaining a projected image of the formation surface of the electrodes and the formation surface of the leads projected onto a plane which intersects the Z axis at right angles;
   ($c_3$) calculating a difference between an image of one of the electrodes and an image of one of the leads in the projected image;
   ($c_4$) calculating a deformation value of at least one of the substrate and the semiconductor chip due to expansion or shrinkage necessary for eliminating the difference;
   ($c_5$) calculating a change in temperature of at least one of the substrate and the semiconductor chip necessary for obtaining the deformation value; and
   ($c_6$) changing the temperature of at least one of the substrate and the semiconductor chip based on the change in temperature.

2. The method of manufacturing a semiconductor device as defined in claim 1,
   wherein, in the step ($c_1$), the formation surface of the electrodes and the formation surface of the leads are imaged at the same time during the imaging.

3. The method of manufacturing a semiconductor device as defined in claim 1,
   wherein, in the step ($c_1$), the imaging is performed by using light in an infrared wavelength region.

4. The method of manufacturing a semiconductor device as defined in claim 1,
   wherein the step ($c_5$) includes calculating an increase in temperature of at least one of the substrate and the semiconductor chip.

5. A manufacturing apparatus for a semiconductor device, the apparatus comprising:
   a stage for disposing a substrate on which a plurality of leads are formed on an XY plane in a three-dimensional coordinate system consisting of XYZ axes;
   a carrier for disposing a semiconductor chip including a plurality of electrodes and the substrate so that a formation surface of the electrodes relatively faces a formation surface of the leads of the substrate with an interval;
   an adjuster for positioning the leads and the electrodes so that the leads and the electrodes respectively face each other; and
   a press for relatively pressing the electrodes against the leads,
   wherein the adjuster includes:
   first means for imaging the formation surface of the electrodes and the formation surface of the leads along an axis which intersects the XY plane at right angles;
   second means for obtaining a projected image of the formation surface of the electrodes and the formation surface of the leads projected onto a plane which intersects the Z axis at right angles;
   third means for calculating a difference between an image of one of the electrodes and an image of one of the leads in the projected image;
   fourth means for calculating a deformation value of at least one of the substrate and the semiconductor chip due to expansion or shrinkage necessary for eliminating the difference;
   fifth means for calculating a change in temperature of at least one of the substrate and the semiconductor chip necessary for obtaining the deformation value; and sixth means for changing the temperature of at least one of the substrate and the semiconductor chip based on the change in temperature.

6. The manufacturing apparatus for a semiconductor device as defined in claim 5,
wherein the first means images the formation surface of the electrodes and the formation surface of the leads at the same time.

7. The manufacturing apparatus for a semiconductor device as defined in claim 5,
wherein the first means performs imaging by using light in an infrared wavelength region.

8. The manufacturing apparatus for a semiconductor device as defined in claim 5,
wherein the fifth means calculates an increase in temperature of at least one of the substrate and the semiconductor chip.

* * * * *